United States Patent
Van Loo et al.

(10) Patent No.: US 9,896,410 B2
(45) Date of Patent: Feb. 20, 2018

(54) PROCESS FOR THE RECOVERY OF BETAINE FROM MOLASSES

(71) Applicant: TIENSE SUIKERRAFFINADERIJ N.V., Brussel (BE)

(72) Inventors: Jan Van Loo, Huldenberg (BE); Wolfgang Wach, Worms (DE)

(73) Assignee: TIENSE SUIKERRAFFINADERIJ N.V., Brussels (BE)

( * ) Notice: Subject to any disclaimer, the term of this patent is extended or adjusted under 35 U.S.C. 154(b) by 0 days.

(21) Appl. No.: 14/358,259

(22) PCT Filed: Nov. 15, 2012

(86) PCT No.: PCT/EP2012/004732
§ 371 (c)(1),
(2) Date: May 15, 2014

(87) PCT Pub. No.: WO2013/072048
PCT Pub. Date: May 23, 2013

(65) Prior Publication Data
US 2014/0295505 A1    Oct. 2, 2014

(30) Foreign Application Priority Data

Nov. 15, 2011 (EP) .................................. 11009055

(51) Int. Cl.

| | | |
|---|---|---|
| C07C 227/40 | (2006.01) | |
| A23K 1/02 | (2006.01) | |
| C12P 19/04 | (2006.01) | |
| A23L 1/09 | (2006.01) | |
| C13B 20/14 | (2011.01) | |
| C13K 1/02 | (2006.01) | |
| C13K 13/00 | (2006.01) | |
| C12P 13/00 | (2006.01) | |
| A23K 10/33 | (2016.01) | |
| A23L 29/30 | (2016.01) | |

(52) U.S. Cl.
CPC ............ *C07C 227/40* (2013.01); *A23K 10/33* (2016.05); *A23L 29/30* (2016.08); *C12P 13/001* (2013.01); *C12P 19/04* (2013.01); *C13B 20/144* (2013.01); *C13K 1/02* (2013.01); *C13K 13/007* (2013.01)

(58) Field of Classification Search
CPC . C07C 227/40; A23L 1/09; A23K 1/02; C12P 19/04
USPC ..... 426/442, 658; 435/101, 267; 252/182.12
See application file for complete search history.

(56) References Cited

U.S. PATENT DOCUMENTS

| | | | | |
|---|---|---|---|---|
| 3,884,714 A | * | 5/1975 | Schneider et al. ........... | 127/46.2 |
| 5,127,957 A | * | 7/1992 | Heikkila et al. ................ | 127/47 |
| 6,331,250 B1 | * | 12/2001 | Kaneko ............. | B01D 15/1828 |
| | | | | 210/198.2 |

FOREIGN PATENT DOCUMENTS

| | | |
|---|---|---|
| EP | 0345511 | 12/1989 |
| EP | 1298204 | 4/2003 |
| EP | 2386649 | 11/2011 |
| JP | 62126951 | 6/1987 |
| JP | 01109000 | 4/1989 |
| JP | 10179200 | 7/1998 |
| WO | 0227037 A1 | 4/2002 |
| WO | 2007071727 | 6/2007 |
| WO | 2011141175 | 11/2011 |

OTHER PUBLICATIONS

Gramblicka et a. 2007. J. Chem. Eng. Data. 52: 345-350.*
International Search Report for PCT/EP2012/004732, Completed by the European Patent Office dated Apr. 15, 2013, 5 Pages.
European Search Report for EP 11009055, Completed by the European Patent Office dated Mar. 20, 2012, 6 Pages.
Ghazi et al. J. Agric. Food Chem. 2006, vol. 54, p. 2964-2968, "Beet Sugar Syrup and Molasses as Low-Cost Feedstock for the Enzymatic Production of Fructo-oligosaccharides."
Norman et al. Denpun Kagaki 1989, vol. 36, No. 2, p. 103-111, "The Production of Frutooligosaccharides from Inulin or Sucrose Using Inulinase or Fructosyltransferase."
Fujisaki et al. Proc. Res. Soc. Jpn. Sugar Refineries Technol. 1989, vol. 37, p. 27-32, English Abstract attached to original document in Japanese, All together 9 Pages.
EP Communication dated Jun. 30, 2016 for EP Appn. No. 12808250.0, 5 pgs.

* cited by examiner

*Primary Examiner* — Hamid R Badr
(74) *Attorney, Agent, or Firm* — Brooks Kushman P.C.

(57) ABSTRACT

A process for the recovery of betaine from a raw material consisting essentially of molasses. The process includes a demineralization step, a conversion step and a separation step. In the demineralization step the overall amount of salts in the molasses is brought to a level lying below 2 wt. % (on overall dry matter). In the conversion step the molasses is subjected to the action of a fructan-forming enzyme, to form a fructan-containing molasses (fructan-molasses). Finally in the separation step, the fructan-molasses is subjected to a chromatographic separation, thereby obtaining a betaine-containing fraction. Whereby the demineralization step is executed prior to the separation step and whereby demineralization step may be executed prior to, during, or subsequent to the conversion step. The raw material may alternatively contain or consist essentially of thick juice.

16 Claims, No Drawings

PROCESS FOR THE RECOVERY OF BETAINE FROM MOLASSES

CROSS-REFERENCE TO RELATED APPLICATION

This application is the U.S. national phase of PCT Application No. PCT/EP2012/004732 filed on Nov. 15, 2012, which claims priority to EP Patent Application No. EP11009055 filed on Nov. 15, 2011, the disclosures of which are incorporated in their entirety by reference herein.

The invention relates to a process for the recovery of betaine from a raw material consisting essentially of molasses.

Such a process is known from U.S. Pat. No. 5,127,957. In the known process, a feed solution of beet molasses is fed into a simulated moving bed chromatographic system. Water is used as eluent. The chromatographic separation leads to the formation of various fractions, a.o. a fraction with increased betaine content and a fraction with increased sucrose content. In Example 1 of U.S. Pat. No. 5,127,957, the fraction with increased betaine content has 70.9 wt. % betaine (on dry matter) and 11.1 wt. % sucrose (on dry matter); the fraction with increased sucrose content has 86.6 wt. % sucrose (on dry matter) and 3.3 wt. % betaine (on dry matter).

A disadvantage of the known process is that the separation of betaine from the other fractions in the molasses is not always optimal.

It is an objective of the present invention to reduce the said disadvantage.

The objective is achieved in that the process comprises:
i. a demineralisation step, in which the overall amount of salts in the molasses is brought to a level lying below 2 wt. % (on overall dry matter);
ii. a conversion step, in which the molasses is subjected to the action of a fructan-forming enzyme, to form a fructan-containing molasses (fructan-molasses);
iii. a separation step, in which the fructan-molasses is subjected to a chromatographic separation, thereby obtaining a betaine-containing fraction, whereby step (i) is executed prior to step (iii), and whereby step (i) may be executed prior to, during, or subsequent to step (ii).

It is an advantage of the process of the present invention that a betaine-containing fraction of high purity can be obtained more efficiently.

It is a further advantage of the process of the present invention that an important further fraction the process, i.e. the fructan-containing fraction as compared to a sucrose-containing fraction in the known process, can have a higher value than the corresponding sucrose-containing fraction of the known process.

Iraj Ghazi et al. disclose in J. Agric. Food Chem., 2006, 54 (8), pp 2964-2968 how sugar syrup and molasses from beet processing were assayed as low-cost and available substrates for the enzymatic synthesis of fructo-oligosaccharides (FOSs). A commercial pectinase (Pectinex Ultra SP-L, from *Aspergillus aculeatus*) characterized by the presence of a transfructosylating activity was used as a biocatalyst.

The process of the invention relates to the recovery of betaine. As meant herein, betaine is used in its meaning of glycine betaine or N,N,N-trimethylglycine, a zwitterion found a.o. in sugar beets (*Beta vulgaris*) and having structural formula (I):

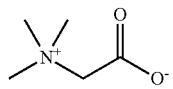

As is known, betaine has a number of functions in mammals, such as being a contributor to osmotic pressure and to function as methyl donor. These functions have led to the circumstance that there is a market for betaine, and it is thus desirable to obtain betaine as a product in an efficient way. One known group of sources of betaine is that of betaine-containing molasses, such as for example sugar beet molasses.

In the process of the present invention, a raw material is used. In a main embodiment, the raw material consists essentially of molasses.

As used herein, the terms 'essentially', 'consist(ing) essentially of', 'essentially all' and equivalents have, unless noted otherwise, in relation to a composition or a process step the usual meaning that deviations in the composition or process step may occur, but only to such an extent that the essential characteristics and effects of the composition or process step are not materially affected by such deviations.

The term molasses as used herein has its common meaning of being a by-product formed in a process for the preparation of sucrose, in particular in the crystallisation stages; furthermore, the molasses as used in the process according to the invention should contain betaine. As used herein, the term molasses refers to the molasses as obtained in the process for the preparation of sucrose, or to a diluted form thereof, whereby the dilution is preferably done with an aqueous phase. The term molasses as meant herein also encompasses a molasses that has been subjected to one or more pre-treatments while still continuing to contain significant amounts of sucrose, betaine, and salts. An example of such a pre-treatment is the reduction of the amount of sucrose by between 10, 20, or 30 and 50, 60, or even 70%; another example of such a pre-treatment is a so-called softening step, aimed at reducing the amount of calcium by at between 10, 20, 30, or 40 and 50, 60, or even 70%. In one embodiment, the molasses is diluted with water; in another embodiment, the molasses is diluted with a vinasse. In one embodiment, the molasses is wholly replaced with a partially fermented vinasse, whereby the vinasse should have a sufficient amount of sucrose in order for the conversion step to take place. Preferably, the molasses is sugar beet molasses. As is known, sugar beet molasses can typically contain, based on total weight of the undiluted and non-pre-treated form: between 45 and 65 wt. % of sucrose; typically between 3 and 8 wt. % of betaine; typically between 6 and 10 wt. % of amino acids, peptides, or proteins; smaller amounts of about 1 wt. % of non-sucrose carbohydrates like fructose and glucose; and a significant amount of other compounds such as organic salts and inorganic salts.

The process according to the invention comprises a demineralisation step (i), in which the overall amount of salts, both organic and inorganic, in the molasses is brought to a level lying below 2 wt. % (on overall dry matter). Demineralisation steps are known as such; one way of executing this step is by means of chromatography, using for example resins such as ion-exchange resins. The demineralisation step may be executed in the form of two subsequent steps, a first 'main' step and a second 'polishing' step. As is known to the person skilled in the art, ion-exchange resins such as strong acid cation exchange resins may be used in demineralisation steps; it is noted hereby that typically the cations in the resin are not primarily present with the purpose of being exchanged, but rather to serve in aiding to achieve a separation of ionic compounds such as salts from non-ionic compounds such as carbohydrates. It is preferred that if cationic resins are used in the demineralisation step (i), the cation form of the resin is primarily a reflection of the main cation or cations as present in the molasses; often in practice, this will mean that resins in potassium and/or sodium form can favourably be used. It was found that in the demineralisation step, betaine typically goes into the fraction of the non-ionic compounds, even though it is a zwitter ion.

Preferably, the overall amount of salts in the molasses is brought to a level lying below 1.5, 1.0, 0.75, 0.60, 0.50, 0.40, 0.30, 0.25, 0.20, 0.15, 0.10, or even below 0.08, 0.05, 0.04, 0.03, 0.02, or 0.01 wt. % of overall dry matter in the molasses. At the same time, any loss of betaine from the molasses into the fraction or fractions containing the salts that are separated off from the molasses should be kept to a minimum. Preferably, at most 40, 35, 30, 25, 20, or even at most 15 or 10 wt. % of the total amount of betaine that entered the demineralistion step (i) is lost into the fraction or fractions containing the salts that are separated off from the molasses. Similarly, the loss of carbohydrates from the molasses into the fraction or fractions containing the salts that are separated off from the molasses should be kept to a minimum. Preferably, at most 40, 35, 30, 25, 20, or even at most 15 or 10 wt. % of the total amount of carbohydrates that entered the demineralistion step (i) are lost into the fraction or fractions containing the salts that are separated off from the molasses.

The limiting of losses of betaine and/or carbohydrates from the molasses in the demineralisation step (i) may be achieved via means that are as such known, such as preferably via the routine optimisation of a chromatographic separation.

It was found that a reduction of the amount of salts in the molasses has a beneficial effect on the efficiency of the separation step (iii), executed later in the process of the invention. Furthermore, it was found that the demineralisation step (i) can have the advantage that food-quality products, i.e. products suitable for human consumption, can be prepared more efficiently.

In the process according to the invention, the molasses is subjected to the action of a fructan-forming enzyme in conversion step (ii). This may be achieved by means as such known. The molasses may be present as such or in diluted form; preferably, the molasses is present in diluted form, the dilution preferably having been done with water. If a certain dilution, or an increase of dilution, leads to a reduction of the efficiency of the enzyme used, then the benefit of dilution should be balanced against the efficiency reduction by the skilled person in routine fashion in order to establish the optimum for the specific circumstances. In one embodiment, the appropriate enzyme is in free form and is thoroughly mixed with the molasses; the enzyme-containing molasses is brought to conditions of temperature and pH such that the enzyme shows appreciable activity. Alternatively, the molasses is first brought to conditions of temperature and pH such that the enzyme can show appreciable activity, followed by the admixture of the enzyme. In another embodiment, the enzyme is available in immobilized form, and the molasses is made to flow along the immobilized enzyme while also having been brought to appropriate conditions of temperature and pH.

The enzyme used in the process according to the invention should be able to catalyse the formation of fructans from sucrose. Free glucose may be formed as by-product.

The term fructan as used herein has its common meaning of being a generic term that relates to a carbohydrate material consisting mainly of fructosyl-fructose links with optionally a glucose starting moiety. The meaning of fructan encompasses the more specific compounds inulin—wherein the fructosyl-fructose links are mainly of the $\beta(2\rightarrow 1)$ type— and levan—wherein the fructosyl-fructose links are mainly of the $\beta(2\rightarrow 6)$ type. Both inulins and levans can be linear or branched, and both can be in polydisperse form, i.e. in the form of a mixture of various degrees of polymerisation, or in homodisperse form.

Inulin is usually polydisperse, i.e. a mixture of compounds of various chain lengths whereby the degree of polymerisation (DP) of the individual compounds can range from 2 to 100 or higher. An individual inulin compound consisting of n fructose moieties is often represented with formula $F_n$, whereas an individual inulin compound having a glucose starting moiety and m fructose moieties is often represented with formula $GF_m$. The term fructo-oligosaccharide—abbreviated as FOS—as used herein indicates a specific form of an inulin material, either monodisperse or polydisperse, whereby the DP of the individual compounds ranges from 2 to 10, in practice often from 2 to 9, or from 2 to 8 or from 2 to 7. Commercially available FOS is usually a polydisperse material having a number-averaged degree of polymerisation ($\overline{DP}$) of about 2 to 5. FOS compounds that were synthesised from sucrose typically consist for the majority of compounds having formula $GF_m$, whereby m is the degree or polymerisation of the compound minus 1.

In practice, FOS is also referred to as oligofructose. As used herein, the terms fructo-oligosaccharide and oligofructose are considered to be synonyms.

The formation of fructan from sucrose may be achieved by selecting an enzyme having fructosyltransferase activity. Such enzymes are as such known, for instance as categorised under enzyme category number EC 2.4.1.99 or EC 2.4.1.9. An early disclosure of such an enzyme is in "The Production of Fructooligosaccharides from Inulin or Sucrose Using Inulinase or Fructosyltransferase from *Aspergillus ficuum*", Barrie E. Norman & Birgitte Højer-Pedersen, Denpun Kagaku vol 36, No. 2, pp 103-111 (1989).

Furthermore, it is known that some β-fructofuranosidases or invertases, i.e. enzymes categorised under EC 3.2.1.26, can also have fructosyltransferase activity and thus could be suitable in the process according to the invention.

Moreover, also enzymes having an endo-inulinase activity—such as enzymes classified under EC 3.2.1.7—may in the presence of sucrose give rise to the formation of fructans such as FOS, in particular if they act in a mixture having a high sucrose content of 40 or 50 wt. % sucrose or higher.

Yet furthermore, enzymes having levansucrase activity— such as enzymes classified under EC 2.4.1.10—can be suitable for use in the method according to the invention.

Also, enzymes having inulin synthase activity, such as for example the enzymes disclosed in EP-A-1298204, can be suitable for use in the method according to the invention.

One example of a preferred enzyme for use in the conversion step of the invention is the endo-inulinase Novozyme 960 (supplier: Novozymes). Another example of a preferred enzyme for use in the conversion step of the invention is Pectinex Ultra SP-L (supplier: Novozymes). It is according to the invention also possible that the enzyme constitutes a combination of two or more enzymes having fructosyltransferase and/or endo-inulinase activity.

In a main embodiment of the invention, the molasses is brought in contact with an enzyme capable of catalyzing the formation of fructo-oligosaccharide (FOS) from sucrose. This main embodiment thus relates to a process according to the invention wherein in the conversion step, the molasses is subjected to the action of an enzyme having endo-inulinase activity and/or fructosyltransferase activity to form a fructo-oligosaccharide-containing molasses (FOS-molasses), and wherein the separation step is executed on the FOS-molasses.

The amount of enzyme needed in the process according to the invention depends on various—as such known—factors such as process temperature, amount of raw materials, pH, allowable process duration, and desired conversion rates. These and other relevant factors may be determined for the process of the invention by the person skilled in the art following the generally accepted procedures in this technical field.

In the process according to the invention, the enzyme is allowed to act on the molasses for a period of time that is sufficiently long to create a fructan-containing molasses, preferably a FOS-containing molasses. The duration of execution of this step according to the invention is mainly chosen in function of the amount of fructan, preferably FOS that is desired. As the skilled person knows, this duration is often in the range between 0.5 or 1 and 72 hours, preferably between 1.5 or 2 and 50 hours, more preferably between 3 or 4 and 36 hours, during which a fructan-containing molasses (fructan-molasses), preferably a FOS-containing molasses (FOS-molasses) is formed.

It is preferred that in the conversion step (ii), between 5 wt. % and 100 wt. % of the sucrose in the molasses is converted. More preferably, at least 10, 20, 30, 40, 50, 60, 70, 80, or 90 wt. % of the sucrose is converted. It is particularly preferred to convert essentially all sucrose. It was found that if the percentage of sucrose that is converted is increased, the subsequent recovery of betaine can be executed more efficiently.

Upon completion of the formation of the fructan-molasses, preferably the FOS-molasses, and in case a free, non-immobilized enzyme was used and mixed into the molasses, it may be desirable to ensure that the enzyme is deactivated. If this is the case, then an enzyme deactivating step may be implemented. The deactivation of the enzyme may be achieved by methods that are as such known and may differ for each specific type of enzyme. An example of such a method of deactivation is an increase in temperature—to a level of for example about 80, 85 or 90° C.—followed by a residence time of between 5 and 30 minutes at such an increased temperature. A further benefit of exposure at such a temperature is that the amounts of any bacteria that may be present are reduced. A further example of a method of enzyme deactivation is a UHT (ultra-pasteurisation) treatment.

It was found that the process of the invention can function when the demineralisation step (i) is done first, then followed by conversion step (ii). However, it was found that the process of the invention can also function when the conversion step (ii) is done first, then followed by the demineralisation step (i). It is contemplated that steps (i) and (ii) may also be executed simultaneously.

In the process of the invention, a separation step (iii) is done on the fructan-molasses. The separation step is executed either during the conversion step or subsequent to the conversion step. Preferably, the separation step is executed subsequent to the conversion step. In the separation step, the fructan-molasses is subjected to a chromatographic separation. As is known, the subjection of a material to a chromatographic separation can lead to the splitting of the material into various fractions. The separation according to the invention should be done such that a betaine-containing fraction is formed. It is known to the person skilled in the art that the particular choice of the stationary phase in the chromatographic separation can influence the performance of the separation. The chromatographic separation may be executed by means that are as such known, such as the passing of the fructan-molasses over a resin.

In a main embodiment of the invention, the separation step is done via the use of resins that are typical for ion-exchange chromatography. As is known, a variety of resins is available for this purpose. In one preferred embodiment of the process of the invention, a strong acid cation exchange resin is chosen. One example of such resins are Styrene-DVB resins, i.e. resins having structures based on styrene copolymerised with divinylbenzene DVB, such as Dowex™ resins.

As was already the case in demineralisation step (i), also in the separation step (iii) the purpose of using ion exchange resins is not primarily to exchange ions—in fact, the fructan-molasses will have a very low amount of ions. Rather, it was found that ion exchange resins can favourably influence the separation efficiency towards obtaining a betaine-containing fraction and optionally other useful fractions. It was also found that if a (strong acid) cation exchange resin is chosen, the choice of cation can influence the separation efficiency. In one embodiment of the invention, cation exchange resins essentially in the sodium form are preferred. In a further embodiment of the invention, cation exchange resins essentially in the potassium form are preferred. In yet a further embodiment of the invention, cation exchange resins essentially in the calcium form are preferred. Further preferred embodiments include resins in magnesium or iron form.

In a main embodiment of the invention, cation exchange resins in mixed form are used; this means that the separation step is done by using a resin system consisting of a mixture of resins in different form, i.e. differing at least in the cation form they are in. Preferred choices of cations in this main embodiment are magnesium, iron, sodium, potassium, and calcium. More preferably, sodium, potassium, and calcium are used.

It was found that an increase of the presence of resins in the calcium form can contribute to an improved separation efficiency of betaine; it was also found, however, that a very high percentage of resin in the calcium form can lead to a situation that the release of betaine from the resins is tailing very far behind the release of all other compounds in the molasses; while this is as such a positive feature as it can allow a direct obtaining of a high-purity betaine-containing fraction, it can also under certain circumstances, for example when the desired purity of the betaine-containing fraction is not extremely high, be a disadvantage in that higher amounts of eluent need to be used. In one preferred embodiment, therefore, a cation exchange resin system is used wherein between 5 and 80 wt. % of the resin system consists of resins in the calcium form; it is then preferred that between 95 and 20 wt. % of the resin system consists of resins in the sodium and/or potassium form. Preferably, between 6, 7, or 8 and 78, 76, 74, 72, or 70, or between 10 and 65 or 60, or between 12 or 14 and 55 or 50, or between 15 and 45 or 40, or between 18, 20 or 22 and 35 or 30 wt. % of the resins in the resin system are in the calcium form. Correspondingly, it is then preferred that between 22, 24, 26, 28, or 30 and 94, 93, or 92, between 35 and 40 and 90, between 45 or 50 and 88 or 86, between 55 or 60 and 85, or between 65 or 70 and 82, 80, or 78 wt. % of the resins in the resin system are then in the sodium and/or potassium form.

In view of the preference of having and maintaining a certain desired cation composition in the abovementioned main embodiment of separation step (iii) of the invention, it follows that the demineralisation step (i) should preferably be executed in such a way, as described in main and preferred embodiments of demineralisation step (i) above, that cations in the molasses are removed to the extent that any remaining cations will not significantly affect the cation composition of the resin system in separation step (iii). Preferably, the demineralisation step (i) is executed such that the fraction or fractions obtained in separation step (iii) has or have, when put into water at 28 wt. %, a conductivity at most 2 mS/cm, preferably at most 1.5, 1, or 0.5 mS/cm. More preferably, the conductivity is even lower with a value of at most 400, 300, 200, or even 100 µS/cm.

As is known in case a resin is used in the separation step, a certain routine optimization may be needed in order to choose the optimal type of resin, e.g. by varying the degree of cross-linking in the resin.

Preferably, the chromatographic separation is done in a simulated moving bed (SMB) system, or further developments of SMB systems such as a Sequential Simulated Moving Bed (SSMB) or an Improved Simulated Moving Bed (ISMB). This has the advantage that the separation step and/or the recovery of a betaine-containing fraction may be done on a continuous basis. In one embodiment, a system is chosen that allows the simultaneous production of multiple fractions, such as the NMCI system.

It was found, surprisingly, that a betaine-containing fraction of high purity can be recovered from a fructan-molasses. Without wishing to be bound to any theory, it is contemplated that the behaviour of fructans, in particular FOS, and possibly also glucose in a chromatographic separation could be such that it exits in a sharper, less diffuse peak than that of sucrose, possibly also influencing thereby the elution behaviour of certain other compounds in favour of obtaining a high-purity betaine.

In the process of the invention, a betaine-containing fraction is obtained. As meant herein, a betaine-containing fraction means a fraction in which the ratio of betaine to the other dry-matter constituents is increased as compared to the fructan-molasses entering the separation step. Preferably, the ratio of betaine to the other dry-matter constituents is increased to at least 25:75, more preferably to 40:60, 50:50, 60:40, 70:30, 80:20, or even to at least 90:10 or 95:5.

The betaine-containing fraction or fractions as obtained in the process of the invention may, if so desired, be processed further by means that are as such known, such as for example by a concentration step in which the amount of eluent is reduced or even brought to essentially zero through means such as evaporation or membrane techniques, possibly followed by a crystallisation step.

The process of the invention can also lead to the obtaining of one or more fructan-containing fractions. One method of obtaining a fructan-containing fraction is by executing the separation step in an SMB system or in related systems designed to obtain multiple product fractions simultaneously from a feed, such as the known NMCI system. Due to the presence of fructans such as preferably FOS, such fractions may have considerable value in various applications such as animal feed or human food.

In one embodiment of the invention, the separated step is operated in such a way that a fructan-containing fraction of very high purity is obtained, combined with a very low to even essentially absent amount of betaine. Preferred in this embodiment are fructan-containing, preferably FOS-containing, fractions having an amount of fructans of at least 70 or 80, or even 90, 95, 98, or even 99 wt. % (as measured on total carbohydrates dry substance), whereby the amount of betaine is at most 0.04 wt. % (as measured on the total dry substance of the fructan-containing fraction), preferably at most 0.03, 0.02, or even at most 0.01 wt. %.

In another embodiment of the invention, however, the separation step is operated in such a way that a fructan-containing fraction is obtained having a favourable combination of fructans with betaine. The invention thus also relates to a converted sugar beet molasses product, containing at least 10 wt. % (as measured on total carbohydrates dry substance) of fructans, preferably fructo-oligosaccharides. Preferably, the converted sugar beet molasses product contains at least 20, 30, 40, 50, 60, 65, 70, 75, or even at least 80 wt. % fructans (as measured on total carbohydrates dry substance), preferably fructo-oligosaccharides. The amount of fructans, preferably fructo-oligosaccharides is preferably at most 98 or 95 wt. % (as measured on total carbohydrates dry substance).

The converted sugar beet product of the invention contains furthermore between 0.05 and 2.0 wt. % betaine (as measured on the total dry substance of the converted sugar beet molasses product). This has the advantage that the nutritional profile of the converted sugar beet product is enhanced in comparison to a product consisting only of fructans. The amount of betaine is preferably between 0.1 and 1.5 wt. % (on total dry matter).

The converted sugar beet product of the invention has a low amount of organic and inorganic salts; this can be achieved if the product is obtained via the process of the invention wherein the demineralisation step is implemented. Preferably, the converted sugar beet product of the invention has, when put into water at 28 wt. %, a conductivity at most 2 mS/cm, preferably at most 1.5, 1, or 0.5 mS/cm. More preferably, the conductivity is even lower with a value of at most 400, 300, 200, or even 100 µS/cm.

The converted sugar beet molasses product of the invention is obtainable, preferably obtained, from a sugar beet molasses having a betaine content of preferably at least 2, 2.5, 3, 3.5, or even 4 wt. % (as measured on the total dry substance of the sugar beet molasses). Preferably, the converted sugar beet molasses product contains at most 25, 20, 15, 10, 5, 4, 3, 2, or even 1 wt. % sucrose (as measured on total carbohydrates dry substance). Preferably, the converted sugar beet molasses product contains at most 1.0, 0.9, 0.8, 0.7, 0.6, or 0.5 wt. % betaine (of total dry matter). Furthermore, the converted sugar beet molasses product contains preferably at most 35, 30, 25, 20, 15, 10, 5, or 4 or 3 or even at most 2.0, 1.5, 1.0, or 0.5 wt. % glucose (as measured on total carbohydrates dry substance). In one embodiment, the converted sugar beet molasses product satisfies the criteria of toothfriendliness; as meant herein, a product is considered to be toothfriendly when the product does not, when tested in the known pH Telemetry test, lead to a decrease of the pH in the mouth to a level of 5.7 or lower.

As noted above, the separation step of the process of the invention can lead to the obtaining of multiple fractions, such as a betaine-containing fraction and a fructan-containing fraction. If the separation step is operated in this fashion, a further fraction will typically also be formed, namely a fraction wherein glucose, having typically been formed in significant amounts during the conversion step, is the main dry-matter contributor.

In an alternative main embodiment of the invention, the process uses not molasses as such but rather thick juice or a mixture of thick juice and molasses as raw material. As used herein, the term thick juice has the meaning it commonly has in the sucrose manufacturing industry of being a liquid stream that is obtained from an evaporation step executed on thin juice. As is known, the term thin juice refers to the purified raw juice that is obtained from an aqueous extraction of sliced sugar beets.

If the raw material for the demineralisation step (i) contains or even consists of thick juice, the amount of carbohydrates, in particular sucrose, will typically be higher as compared to the situation wherein the raw material consists essentially of molasses. Otherwise, however, the steps of the invention can be executed as described above. If a mixture of thick juice and molasses is used as raw material, the ratio between thick juice and molasses preferably varies between 5:95 and 95:5, more preferably between 30:70 and 70:30.

The process of the invention will be illustrated by means of the following Example, whereby the Example should not be interpreted as limiting the scope of the invention.

EXAMPLE 1

Demineralisation Step

A decalcified sugar beet molasses (solids content 60 Brix) was subjected to a demineralisation by means of chromatography in an ISMB. The solid phase in the chromatography columns was an cation exchange resin system (Dowex™ 99/320), partly in potassium and partly in sodium form. The total resin volume was 9.04 L, the eluate was water, the ratio eluate/molasses was 5.5, the flow rate was 0.5 bed volume (BV) per hour, the temperature was 80° C.

The composition of the molasses as fed into the ISMB is given in Table 1. The ISMB was set up so as to obtain two fractions: a salts-enriched fraction, and a product fraction having as little salts as possible. The composition of these two fractions is given in Table 2.

TABLE 1

| | Feed (wt. % of total dry matter) |
|---|---|
| Sucrose | 62.9 |
| Betaine | 6.67 |
| Salts | 25.3 |

TABLE 2

| | Salts-enriched fraction (wt. % of total dry matter) | Product fraction (wt. % of total dry matter) |
|---|---|---|
| Sucrose | 29.82 | 88.11 |
| Betaine | 0.48 | 10.51 |
| Salts | 59.41 | 0.0 |

Conversion Step

The product fraction as obtained from the demineralisation step was subjected to a conversion step. In this conversion step, the product fraction was brought into contact with Novozymes 960, an endo-inulinase. This was done at a pH of 6.4, a temperature of 56° C., for a 24 hour period. The composition of the resulting converted product fraction is given is given in Table 3.

TABLE 3

| Compound | Concentration (wt. % on total dry matter) |
|---|---|
| Sucrose | 5.1 |
| Betaine | 6.54 |
| FOS | 50.15 |
| Glucose | 32.1 |
| Fructose | 2.63 |
| Others | 3.48 |

Separation Step

The converted product fraction as obtained in the conversion step was subjected to a separation step. This step was executed in an NMCI (New MCI, originally developed by Mitsubishi Chemical Co and Nippon Rensui Co); the resin system used consisted of Dowex™ 99/320, whereby 20 wt. % of the resin was in the calcium form, and 80 wt. % of the resin was in the potassium form. The NMCI was set up so as to obtain three fractions: a FOS fraction, a betaine fraction, and a sugars fraction. The main operating conditions were: temperature 60° C., flow rate 0.5 BV/h, ratio eluent (water)/converted product fraction 7.01. The composition of the resulting three fractions is given in Table 4.

TABLE 4

| | Concentration (wt. % on total dry matter) | | |
|---|---|---|---|
| Compound | Sugars fraction | Betaine fraction | FOS fraction |
| Sucrose | 3.68 | 0.0 | 6.86 |
| Betaine | 0.15 | 89.53 | 1.53 |
| FOS | 9.63 | 9.75 | 87.51 |
| Glucose | 74.80 | 0.00 | 1.85 |
| Fructose | 6.21 | 0.72 | 0.0 |
| Others | 5.53 | 0.0 | 2.26 |

As is clear from Table 4, a betaine fraction of high purity was obtained; this purity is sufficient for use of the product in animal feed applications. Furthermore, the FOS fraction as obtained is a converted sugar beet molasses product according to the invention.

The invention claimed is:

1. Process for recovery of betaine from a raw material consisting essentially of molasses, comprising:
   (i) a demineralisation step, in which the overall amount of salts in the molasses is brought to a level lying below 2 wt. % (on overall dry matter);
   (ii) a conversion step, in which the molasses is subjected to action of a fructan-forming enzyme, to form a fructan-containing molasses (fructan-molasses); and
   (iii) a separation step, in which the fructan-molasses is subjected to a chromatographic separation, thereby obtaining a betaine-containing fraction in which a ratio of betaine to other dry matter constituents is increased to at least 90:10,
       whereby step (i) is executed prior to step (iii), and whereby step (i) may be executed prior to, during, or subsequent to step (ii), and
   wherein in separation step (iii) a strong acid cation exchange resin system is used consisting of resins, whereby between 20 and 95% are resins in sodium or potassium form, and between 5 and 80% are resins in calcium form.

2. The process according to claim 1, wherein in the demineralisation step the overall amount of salts is reduced to at most 0.5 wt. % on overall dry matter.

3. The process according to claim 1, wherein the fructan-forming enzyme is selected from the group consisting of: enzymes having endo-inulinase activity, enzymes having fructosyltransferase activity, and mixtures thereof.

4. The process according to claim 1, wherein the demineralisation step (i) is executed as a chromatographic separation, whereby a strong acid cation resin is used as solid phase in the chromatographic separation.

5. The process according to claim 1, wherein in the conversion step, the molasses is subjected to the action of an enzyme having endo-inulinase activity and/or fructosyltransferase activity to form a fructo-oligosaccharide-containing molasses (FOS-molasses), and wherein the separation step is executed on the FOS-molasses.

6. The process according to claim 1, wherein the separation step is executed in a simulated moving bed (SMB) chromatography system.

7. The process according to claim 1, wherein in the separation step in addition to the betaine-containing fraction also a fructan-containing fraction is obtained.

8. The process according to claim 1, wherein the raw material contains or consists essentially of thick juice.

9. A method of producing a food or an animal feed product from a process for recovery of betaine from a raw material consisting essentially of molasses, the method comprising:
  (i) a demineralisation step, in which the overall amount of salts in the molasses is brought to a level lying below 2 wt. % (on overall dry matter);
  (ii) a conversion step, in which the molasses is subjected to action of a fructan-forming enzyme, to form a fructan-containing molasses (fructan-molasses);
  (iii) a separation step, in which the fructan-molasses is subjected to a chromatographic separation, thereby producing a betaine-containing fraction in which a ratio of betaine to other dry matter constituents is increased to at least 90:10,
    whereby step (i) is executed prior to step (iii), and whereby step (i) may be executed prior to, during, or subsequent to step (ii), and
    wherein in separation step (iii) a strong acid cation exchange resin system is used consisting of resins, whereby between 20 and 95% are resins in sodium or potassium form, and between 5 and 80% are resins in calcium form; and
  (iv) using the betaine-containing fraction as an additive in a preparation of a food or an animal feed product.

10. The process according to claim 1, wherein the betaine-containing fraction has at least 30 wt. % fructans, as measured on total carbohydrate dry matter.

11. The process according to claim 1, wherein the separation step is operated in such a way that a high purity fructan-containing fraction is obtained, the high purity fructan-containing fraction having an amount of fructans of at least 90 wt. % as measured on total carbohydrates dry substance with an amount of betaine that is at most 0.04 wt. as measured on the total dry substance of the fructan-containing fraction.

12. The process according to claim 11 wherein the high purity fructan-containing fraction has an amount of betaine that is at most 0.01 wt. % as measured on the total dry substance of the fructan-containing fraction.

13. The process according to claim 11 wherein the high purity fructan-containing fraction includes fructo-oligosaccharides.

14. The process according to claim 1, wherein the separation step is operated in such a way that a high purity fructan-containing fraction is obtained, the high purity fructan-containing fraction having an amount of fructans of at least 95 wt. % as measured on total carbohydrates dry substance with an amount of betaine that is at most 0.02 wt. as measured on the total dry substance of the fructan-containing fraction.

15. The process according to claim 14 wherein the high purity fructan-containing fraction has an amount of betaine that is at most 0.01 wt. % as measured on the total dry substance of the fructan-containing fraction.

16. The process according to claim 15 wherein the high purity fructan-containing fraction includes fructo-oligosaccharides.

* * * * *